(12) United States Patent
Lopez et al.

(10) Patent No.: US 9,987,036 B2
(45) Date of Patent: Jun. 5, 2018

(54) SYSTEM AND METHOD FOR POWERING AN ULTRASONIC SURGICAL DEVICE

(71) Applicant: COVIDIEN LP, Mansfield, MA (US)

(72) Inventors: John T. Lopez, Boulder, CO (US); Matthew A. Schaning, Cambridge, WI (US)

(73) Assignee: COVIDIEN LP, Mansfield, MA (US)

( * ) Notice: Subject to any disclaimer, the term of this patent is extended or adjusted under 35 U.S.C. 154(b) by 341 days.

(21) Appl. No.: 14/865,028

(22) Filed: Sep. 25, 2015

(65) Prior Publication Data

US 2016/0095616 A1 Apr. 7, 2016

Related U.S. Application Data

(60) Provisional application No. 62/059,705, filed on Oct. 3, 2014.

(51) Int. Cl.
| | |
|---|---|
| *H01L 41/09* | (2006.01) |
| *A61B 17/32* | (2006.01) |
| *A61B 17/29* | (2006.01) |
| *A61B 17/00* | (2006.01) |

(52) U.S. Cl.
CPC .. *A61B 17/320092* (2013.01); *A61B 17/2909* (2013.01); *A61B 2017/0046* (2013.01); *A61B 2017/00734* (2013.01)

(58) Field of Classification Search
USPC .......................................... 310/317; 29/25.35
See application file for complete search history.

(56) References Cited

U.S. PATENT DOCUMENTS

| | | | |
|---|---|---|---|
| 5,230,704 | A | 7/1993 | Moberg et al. |
| 5,282,800 | A | 2/1994 | Foshee et al. |
| 5,480,398 | A | 1/1996 | Eggers |
| 5,578,056 | A | 11/1996 | Pauldrach |
| 6,007,560 | A | 12/1999 | Gottlieb et al. |
| 6,162,194 | A | 12/2000 | Shipp |
| 6,325,795 | B1 | 12/2001 | Lindemann et al. |
| 6,432,047 | B1 | 8/2002 | Gust et al. |
| 8,177,787 | B2 | 5/2012 | Walker et al. |
| 8,956,341 | B2 | 2/2015 | Chen et al. |
| 9,011,471 | B2 | 4/2015 | Timm et al. |
| 9,113,897 | B2 | 8/2015 | Deborski et al. |

*Primary Examiner* — Thomas Dougherty

(57) ABSTRACT

An ultrasonic surgical instrument includes a housing, an ultrasonic transducer and generator assembly disposed in the housing, a shaft extending from a distal end of the housing, and an end effector assembly coupled to the shaft and operatively connected to the ultrasonic transducer and generator assembly. The ultrasonic surgical instrument further includes a handle assembly having a first set of power contacts formed thereon and being removably attachable to the housing, a power receiving mechanism having a second set of power contacts formed thereon, and a power cable electrically connected between the first and second power contacts.

20 Claims, 10 Drawing Sheets

SYSTEM AND METHOD FOR POWERING AN ULTRASONIC SURGICAL DEVICE

CROSS REFERENCE TO RELATED APPLICATION

The present application claims the benefit of and priority to U.S. Provisional Application Ser. No. 62/059,705, filed on Oct. 3, 2014, the entire contents of which are incorporated herein by reference.

BACKGROUND

1. Technical Field

The present disclosure relates to a system and method for powering an ultrasonic surgical instrument via a power cable.

2. Background of Related Art

A typical battery pack for a battery-powered device includes one or more battery cells coupled to one another via a powering circuit that provides electrical power to the device. Battery packs have been developed that include control and safety circuitry configured to monitor various characteristics of the battery cells, both collectively and individually, e.g., individual battery cell voltage, battery pack voltage, temperature, and/or current, such that conditions that may cause failure or damage to the individual battery cells, the battery pack, and/or the device, e.g., as a result of over-voltage, under-voltage, over-temperature, or over-current, may be averted.

Control and safety circuitry is also utilized to detect battery cell failure, for example, by detecting excessive internal self-discharge, atypical impedance, or state of charge curve anomalies. However, in some instances, especially concerning emerging markets, rechargeable battery packs may not be easily accessible, and if they are accessible, may not be autoclavable.

Therefore, a need exists for an alternative to using rechargeable battery packs in ultrasonic surgical instruments.

SUMMARY

In accordance with aspects of the present disclosure, an ultrasonic surgical instrument is presented including a housing, an ultrasonic transducer and generator assembly disposed in the housing, a shaft extending from a distal end of the housing, and an end effector assembly coupled to the shaft and operatively connected to the ultrasonic transducer and generator assembly. The ultrasonic surgical instrument further includes a handle assembly having a first set of power contacts formed thereon and being removably attachable to the housing, a power receiving mechanism having a second set of power contacts formed thereon, and a power cable electrically connected between the first and second power contacts.

According to an aspect of the present disclosure, a waveguide is mechanically coupled to the ultrasonic transducer and generator assembly and disposed in the shaft, the waveguide being adapted to transmit current from the power cable to the end effector assembly.

According to a further aspect of the present disclosure, a microcontroller and a buck converter are operatively connected to the ultrasonic transducer and generator assembly. The buck converter is a DC-DC converter board incorporating a synchronous two-phase buck converter. The buck converter also receives an unregulated DC voltage from the power cable and supplies a regulated and reduced DC output voltage to the ultrasonic transducer and generator assembly. The microcontroller provides a pulse width modulation signal to the buck converter to regulate current supplied to the ultrasonic transducer and generator assembly via the power cable.

According to a further aspect of the present disclosure, the power receiving mechanism includes an AC/DC transformer.

In a further aspect of the disclosure, a clamp trigger is operatively associated with the end effector assembly.

In yet a further aspect of the disclosure, an activation button is operatively connected to the ultrasonic transducer and generator assembly.

According to a further aspect of the disclosure, the ultrasonic transducer and generator assembly is configured to be autoclavable.

According to yet a further aspect of the disclosure, a method of performing a surgical procedure is presented. The method includes the step of accessing an underlying operative site with an ultrasonic surgical instrument, including a housing, an ultrasonic transducer and generator assembly disposed in the housing, a shaft extending from a distal end of the housing, and an end effector assembly coupled to the shaft and operatively connected to the ultrasonic transducer and generator assembly. The ultrasonic surgical instrument further includes a handle assembly having a first set of power contacts formed thereon and being removably attachable to the housing, a power receiving mechanism having a second set of power contacts formed thereon, and a power cable electrically connected between the first and second power contacts.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the subject instrument are described herein with reference to the drawings wherein.

DETAILED DESCRIPTION

Figure 1:
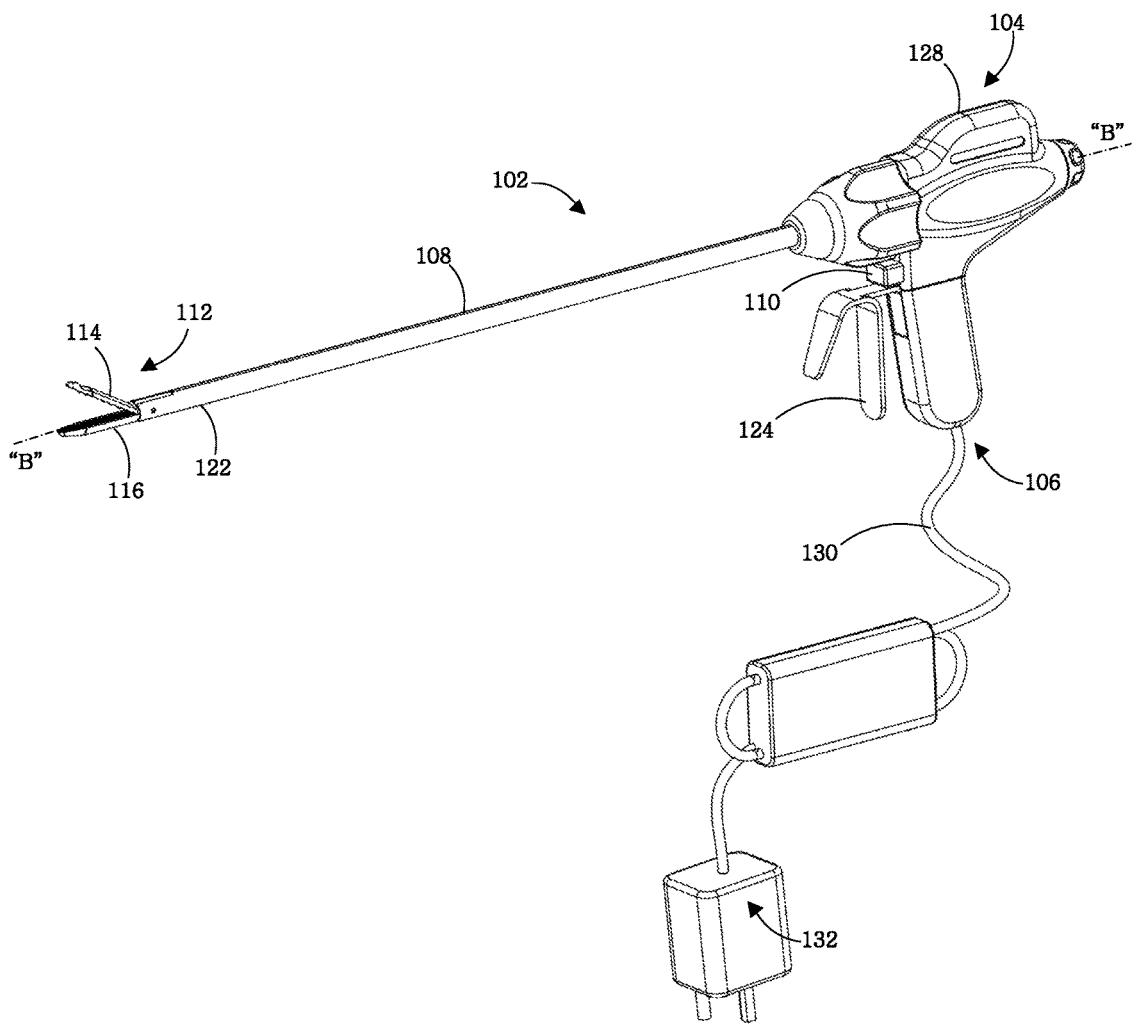
FIG. 1 is a side, perspective view of an ultrasonic surgical instrument, in accordance with embodiments of the present disclosure.

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

As used herein, the term "distal" and "proximal" are with respect to the medical professional utilizing the device or component, with proximal being nearer to the medical professional either when in use or during insertion into the patient.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Referring to FIG. 1, ultrasonic instrument 102 includes a housing 104, an ultrasonic transducer and generator assembly 128 (TAG 128) having a contact connector 160, a handle assembly 106, a shaft 108, and an end effector assembly 112. Housing 104 is configured to releasably engage TAG 128 and handle assembly 106. Shaft 108 extends distally from housing 104 to define longitudinal axis "B-B" and includes end effector assembly 112 disposed at distal end 122 thereof. A pair of jaw members 114 and 116 are mounted on end effector assembly 112 such that one or both of jaw members 114 and 116 of end effector assembly 112 are movable relative to one another, e.g., upon actuation of movable handle 124, between an open position and a clamped position for grasping tissue therebetween. Further, one of the jaw members, e.g., jaw member 116, serves as an active or oscillating ultrasonic blade that is selectively activatable to ultrasonically treat tissue grasped between jaw members 114, 116.

The transducer portion (not shown) of TAG 128 is configured to convert electrical energy provided by a power receiving mechanism 132 into mechanical energy that produces motion at the active jaw member 116. More specifically, the electronics (not explicitly shown) of the TAG 128 convert the electrical energy provided by power receiving mechanism 132 into a high voltage AC waveform that drives the transducer. When the transducer and the waveguide are driven at their resonant frequency, mechanical, e.g., ultrasonic vibration, motion is produced at the active jaw member 116 for treating tissue grasped between jaw members 114, 116. Further, an activation button 110 disposed on housing 104 is selectively activatable to operate instrument 102 in two modes of operation, that is, a low-power mode of operation and a high-power mode of operation.

The handle assembly 106 is connected to a power cable 130, which in turn is connected to power receiving mechanism 132. The power receiving mechanism 132 may be a plug, as will be described in detail below.

Figure 2:
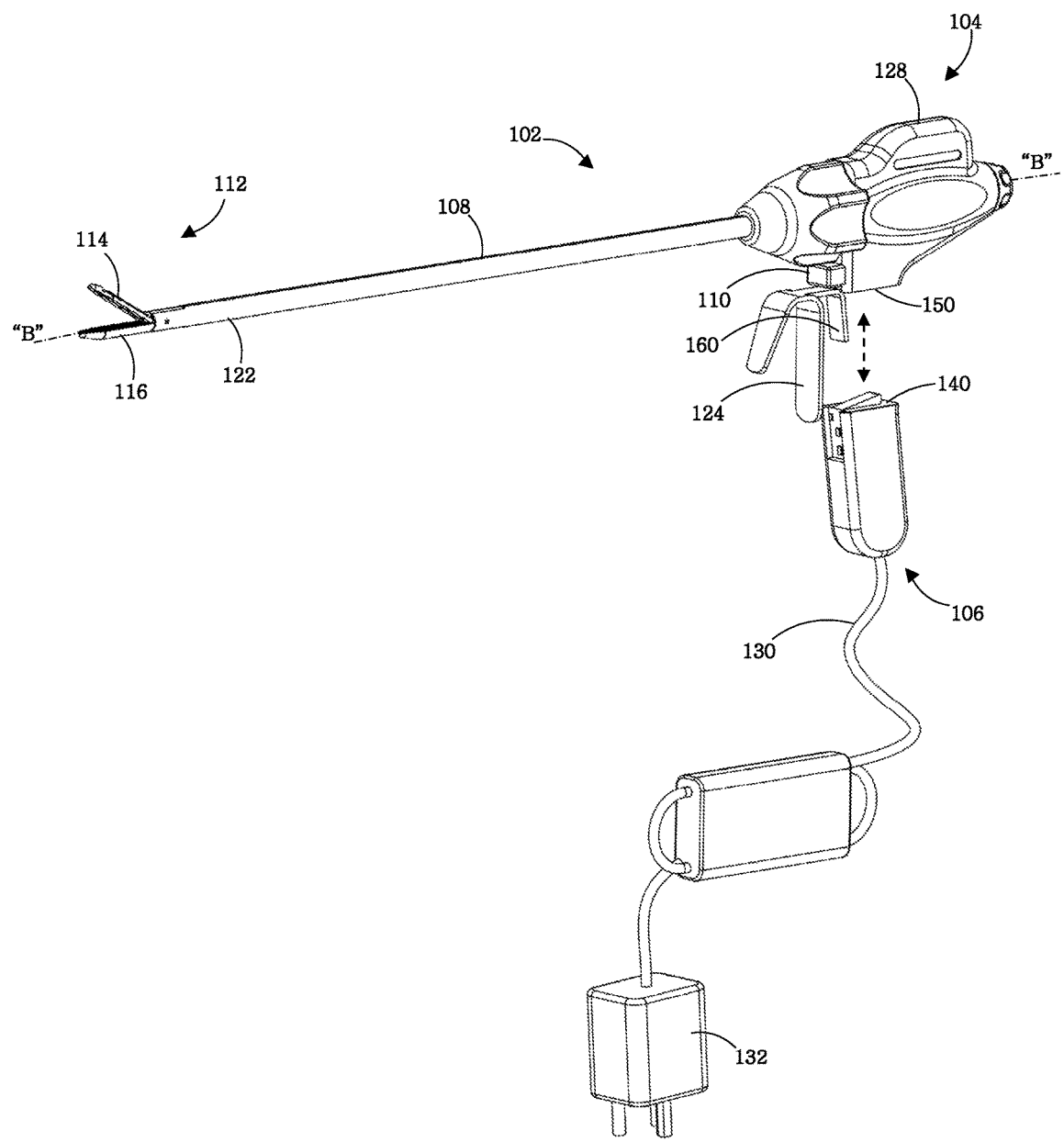
FIG. 2 is a side, perspective view of the ultrasonic surgical instrument of FIG. 1, where the handle assembly is detached from the ultrasonic transducer and generator assembly, in accordance with an embodiment of the present disclosure.

FIG. 2 illustrates how the handle assembly 106 is detached from TAG 128. As shown, a top portion 140 of the handle assembly 106 is disconnected from a bottom portion 150 of housing 104. Handle assembly 106 may be detached from TAG 128 in a slidable manner. Alternatively, handle assembly 106 may be detached from TAG 128 via a snap mechanism. One skilled in the art may contemplate a plurality of different configurations for connecting and disconnecting handle assembly 106 from TAG 128.

Figure 3A:
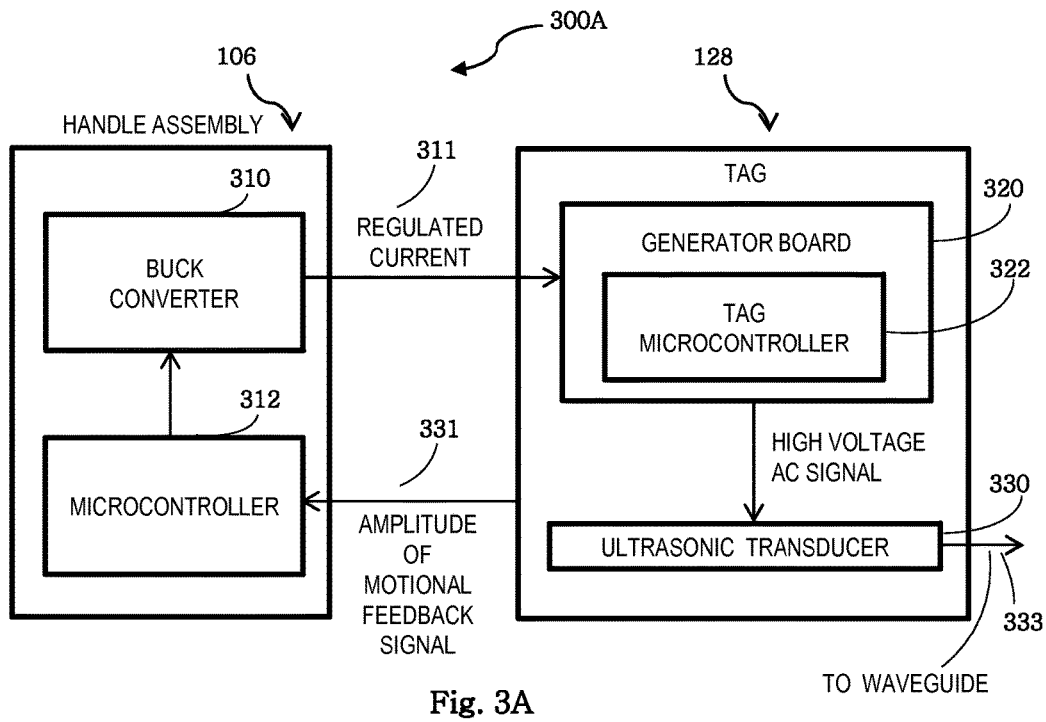
FIG. 3A is a schematic block diagram of the system architecture of the ultrasonic surgical instrument of FIG. 1, where a buck converter is incorporated in the handle assembly, in accordance with an embodiment of the present disclosure.

FIG. 3A is a schematic block diagram 300A of one embodiment of the system architecture of the ultrasonic surgical instrument of FIG. 1, where a buck converter 310 and a microcontroller 312 are incorporated in the handle assembly 106, in accordance with an embodiment of the present disclosure.

The TAG 128 includes a generator board 320 having a TAG microcontroller 322 and an ultrasonic transducer 330. The TAG 128 applies mechanical motion from the ultrasonic transducer 330 to the waveguide 333.

The TAG 128 and operational elements of handle assembly 106 communicate over a serial data link to coordinate their operation. The microcontroller 312 regulates the current 311 output from the buck converter 310 to control the buck converter 310 based on the motional feedback 331 received from the TAG 128. The buck converter 310 reduces and regulates the voltage to provide a DC Voltage to the TAG 128. The TAG 128 uses the DC voltage to generate the high voltage AC signal that is applied to the ultrasonic transducer 330.

The microcontroller 312 performs an amplitude proportional-integral-derivative ("PID") control algorithm 413 to regulate the current 311 supplied to the TAG 128 to achieve and maintain a desired amplitude of the motional feedback signal 331. The amplitude of the motional feedback signal 331 corresponds to the amplitude of the mechanical motion of the ultrasonic transducer 330. The microcontroller 312 also handles the user interface and monitors the power delivered via the power receiving mechanism 132 during operation of the ultrasonic surgical device 102.

The TAG microcontroller 322 controls the conversion of the DC voltage from the handle assembly 106 to the high voltage AC signal applied to the ultrasonic transducer 330. The TAG microcontroller 322 also controls the amplitude and frequency of the high voltage AC signal used to drive the ultrasonic transducer 330.

The buck converter 310 includes a buck converter board (not shown), which is a DC-to-DC converter board that incorporates a two-phase buck converter. The buck converter board receives an unregulated DC voltage and regulates and reduces it to a DC output voltage for the TAG 128. The microcontroller 312 provides two pulse-width modulation signals to the buck converter 310 to regulate the current of the DC voltage supplied to the generator 128.

Figure 3B:
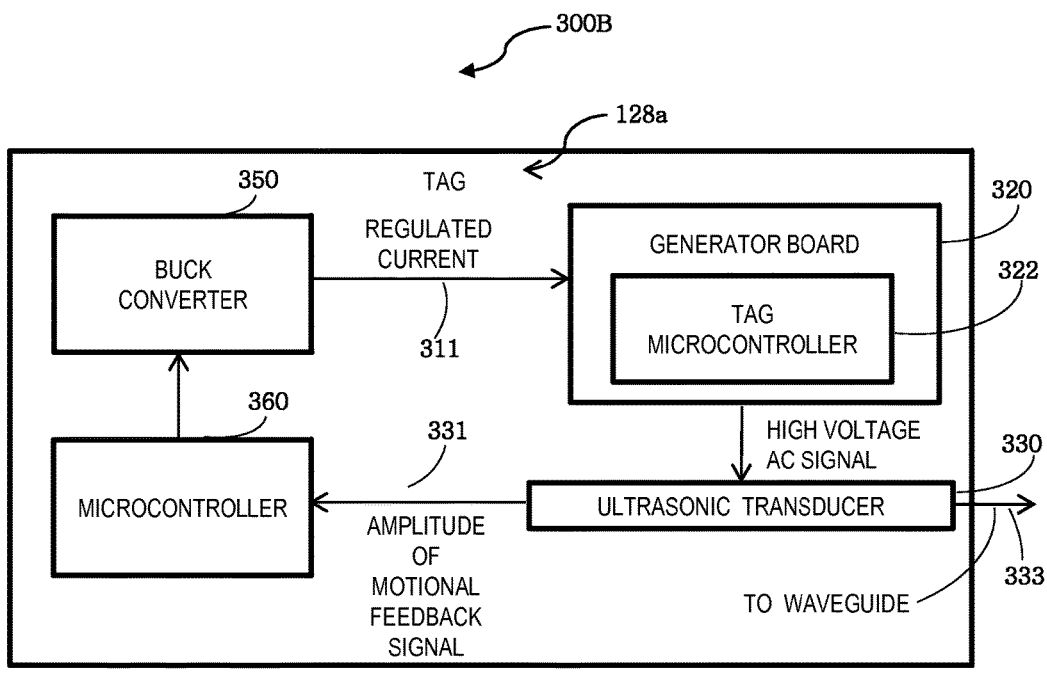
FIG. 3B is a schematic block diagram of the system architecture of the ultrasonic surgical instrument of FIG. 1, where a buck converter is incorporated in the ultrasonic transducer and generator assembly, in accordance with an embodiment of the present disclosure.

FIG. 3B is a schematic block diagram 300B of another embodiment of a system architecture of the ultrasonic surgical instrument of FIG. 1, where the buck converter 350 and the microcontroller 360 are incorporated in the TAG 128a. The operations between the buck converter 350 and the microcontroller 360, and the TAG 128a are similar to those described above with reference to FIG. 3A.

Figure 4A:
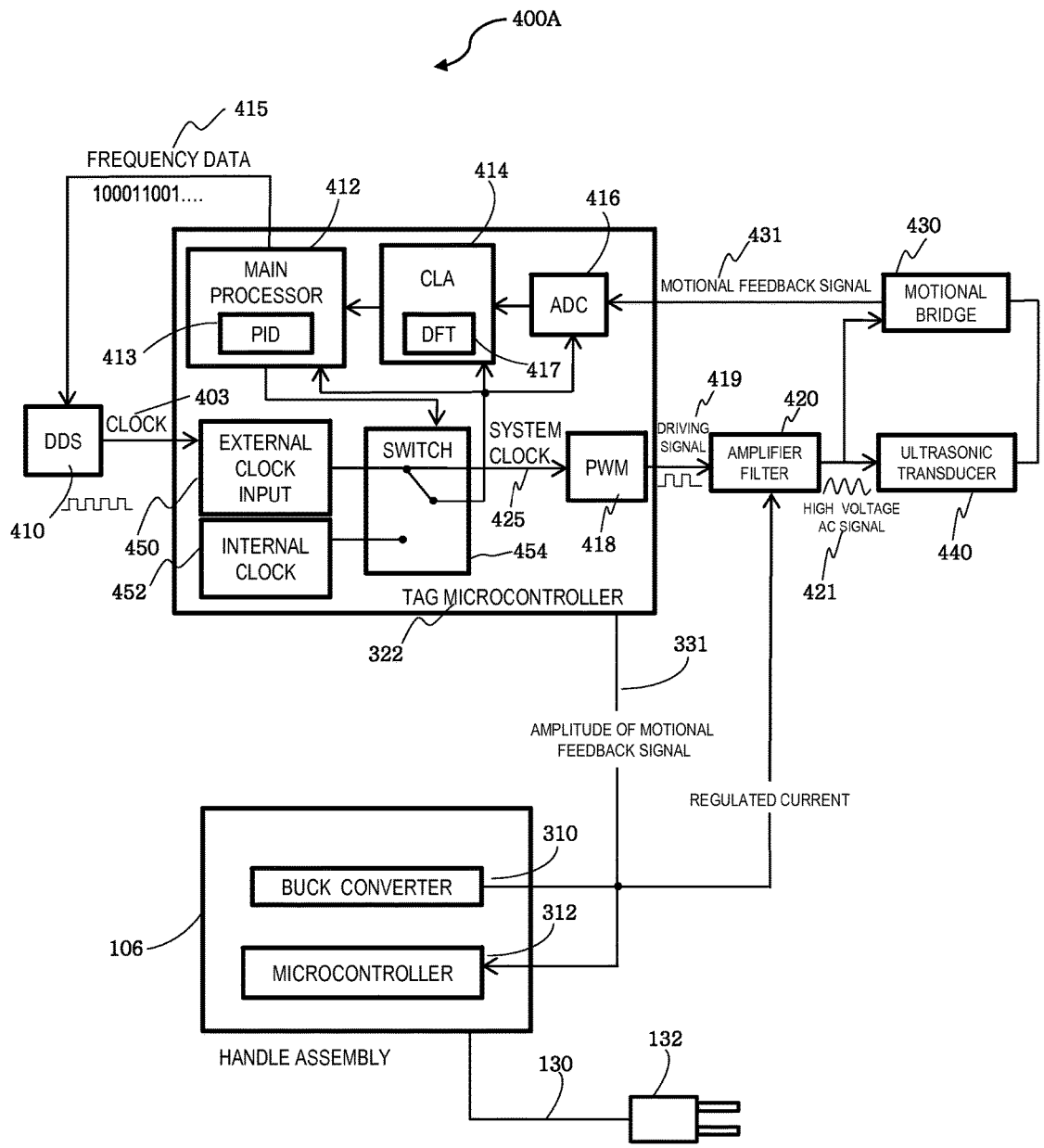
FIG. 4A is a schematic diagram of the ultrasonic transducer and generator assembly, where the buck converter is incorporated in the handle assembly, in accordance with an embodiment of the present disclosure.

FIG. 4A depicts a schematic diagram 400A of the surgical instrument embodiment where the buck converter is incorporated in the handle assembly as in the embodiment of FIG. 3A, in accordance with an embodiment of the present disclosure.

The TAG 128 controls the frequency of the ultrasonic vibrations in the ultrasonic transducer by controlling the frequency of a high voltage AC signal 421 applied to an ultrasonic transducer 440 and received from an amplifier filter 420.

The TAG microcontroller 322 includes a main processor 412, a control law accelerator 414 ("the CLA"), and an analog-to-digital ("A/D") converter 416. The TAG microcontroller 322 also includes an external clock input 450, an internal oscillator 452, and a switch 454 that switches the system clock between an external clock input 450 which is received from a clock signal 403 outputted from the DDS and the internal oscillator 452. The system clock drives the main processor 412, the CLA 414, and the A/D converter 416.

The internal oscillator 452 of the TAG microcontroller 322 generates a system clock signal 425. The TAG microcontroller 322 then generates a driving signal 419 based on the clock signal 425. The driving signal 419 is outputted from the pulse width modulator 418. When the clock signal 403 is provided to the external clock input 450 of the TAG microcontroller 322, the TAG microcontroller 322 switches the system clock 425 from the internal clock 452 to the clock signal 403.

During normal operation, the TAG microcontroller 322 adjusts frequency data 415 of the driving signal 419 by adjusting the clock signal 403. The TAG microcontroller 322 generates a driving signal 419 having a frequency that is in a predetermined and fixed relationship with the system clock 425. A direct digital synthesizer "DDS" 410 controls the system clock 425. As such, the driving signal 419 is also in a predetermined and fixed relationship with the clock signal 403 from the DDS 410. That is, the frequency of the driving signal 419 only changes when the clock frequency generated by the DDS 410 changes. Therefore, the frequency of the ultrasonic vibration is indirectly controlled by the frequency of the clock signal 403 from the DDS 410, which is adjusted by the Frequency Data 415 from the main processor 412.

The motional bridge 430 measures the mechanical motion of the ultrasonic transducer 440 and provides to the TAG microcontroller 322 a motional feedback signal 431 representing the mechanical motion of the ultrasonic transducer 440. The TAG microcontroller 322 samples the motional feedback signal 431 using an A/D converter 416. Using the sampled motional feedback signal 431, the TAG microcontroller 322 generates Frequency Data 415, which causes the DDS 410 to adjust its clock signal 403, which results in an adjustment of the frequency of the driving signal 419 in an effort to achieve and maintain resonance of the ultrasonic transducer 440. At resonance, the driving signal 419 is in phase with the motional feedback signal 431.

The CLA 414 receives samples of the motional feedback signal 431 from the A/D converter 416 and performs a Discrete Fourier Transform (DFT) algorithm 417 on the samples to obtain phase information of the motional feedback signal 431. Then, the CLA 414 communicates the phase information to the main processor 412. As described above, the main processor 412 uses the phase information to adjust the frequency of the clock signal 403 output from the DDS 410, which determines the frequency of the driving signal 419.

The DDS 410 is a fully integrated circuit and includes a phase accumulator, a sine look-up table, and a 10-bit D/A converter. The TAG microcontroller 322 loads digital frequency data into a frequency register of the DDS 410, which the DDS 410 uses to update the frequency of the clock signal 403. The clock signal 403 is fed to the TAG microcontroller 322.

Figure 4B:
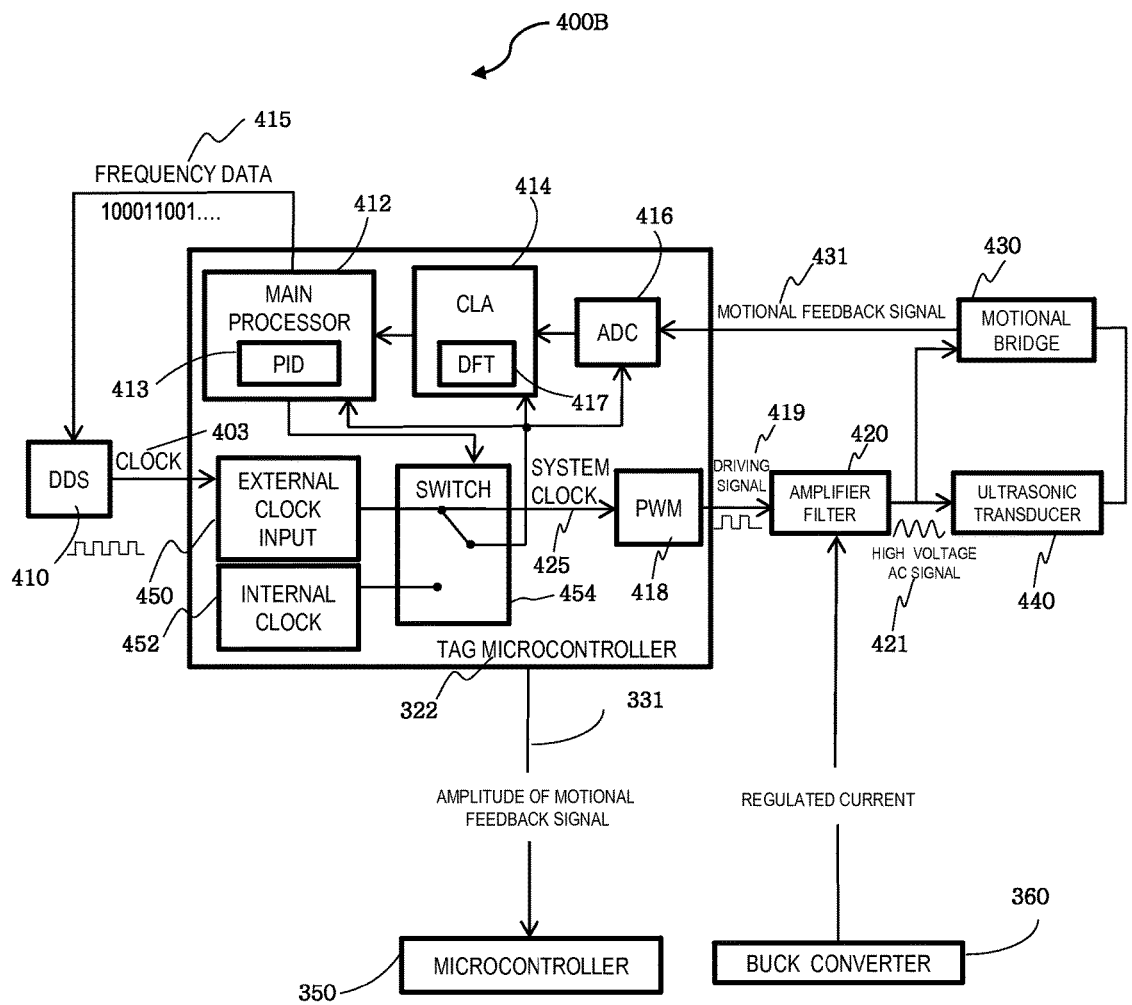
FIG. 4B is a schematic diagram of the ultrasonic transducer and generator assembly incorporating the buck converter therein, in accordance with an embodiment of the present disclosure.

FIG. 4B is a schematic diagram 400B of the ultrasonic transducer and generator assembly incorporating the buck converter therein as shown in FIG. 3B, in accordance with an embodiment of the present disclosure. The operations between the buck converter 350 and the microcontroller 360, and the TAG 128 are similar to those described above with reference to FIG. 4A.

Figure 5:
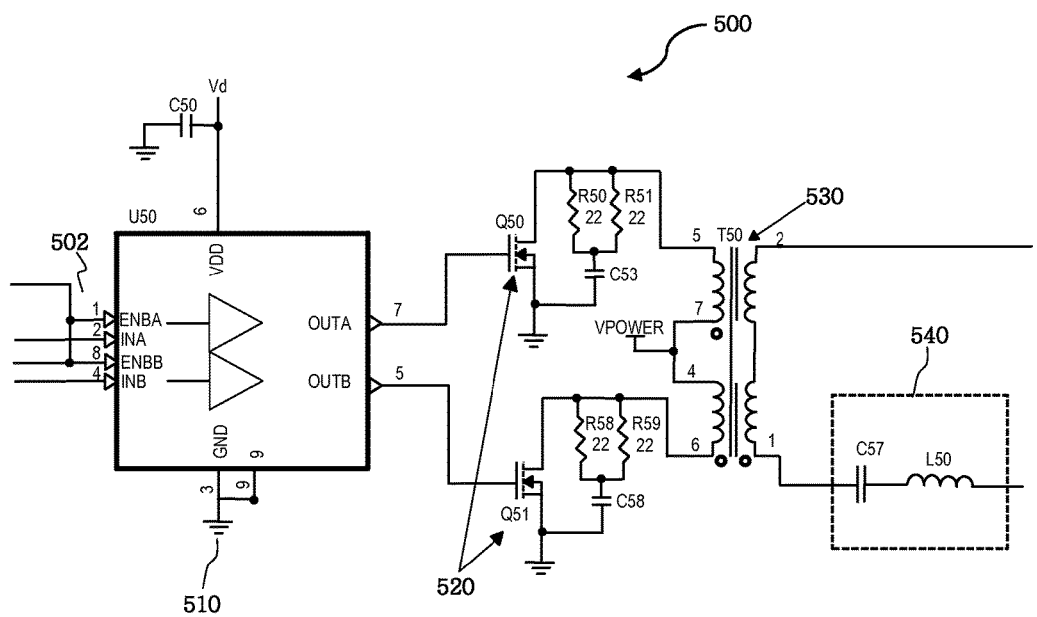
FIG. 5 is a schematic diagram of an amplifier/filter circuit, according to one aspect of the present disclosure.

FIG. 5 is a schematic diagram of an amplifier/filter circuit 500, according to one aspect of the present disclosure. The amplifier/filter circuit 500 converts the DC voltage 502 received from the handle assembly 106 into a high voltage square wave in accordance with the driving signal 419 from the TAG microcontroller 322 (see FIGS. 4A and 4B). The amplifier/filter 500 then filters the high voltage square wave to obtain a high voltage AC signal (a sine wave), which is applied to the ultrasonic transducer 440. The amplifier/filter circuit 500 receives the driving signal 419 generated by the TAG microcontroller 322 via two channels ("CHA" and "CHB"). The driving signal comprises two voltage signals that are 180° out of phase with each other.

The FET drivers 510 amplify each voltage signal to drive their respective output power FET 520 ("Q1" or "Q2"). The output power FETs 520 are switched 180° out of phase in accordance with the driving signal 419 from the TAG microcontroller 322. In other words, the first output power FET Q1 is switched on for the first half of the driving signal period and the second output power FET Q2 is switched on for the second half of the driving signal period. The switching of the output power FETs in combination with the DC voltage induces an AC signal in the primary side of the transformer 530.

The DC voltage output from the buck converter 310 is fed to the "$V_{out}$" terminal of the transformer ("T1"). The $V_{out}$ terminal of the transformer is the center-tap of the primary side of the transformer T1 (i.e., the single inductor symbol shown on the left side of the transformer T1). The AC signal induced in the primary side of the transformer induces a high-voltage square wave driving signal on the secondary side of the transformer T1 (i.e., the two inductor symbols shown on the right side of the transformer T1). The high-voltage square wave is then filtered by an output filter inductor 540 resulting in a high-voltage AC signal, which is applied to the ultrasonic transducer 440.

Figure 6:
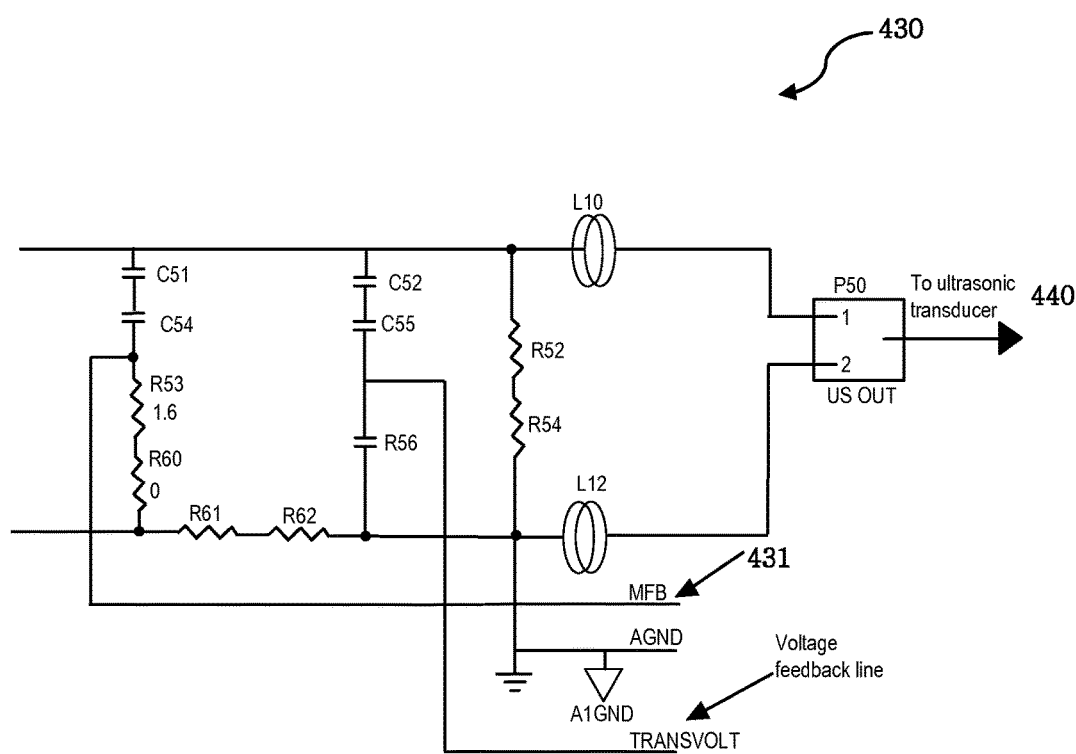
FIG. 6 is a schematic diagram of a motional bridge, according to one aspect of the present disclosure.

FIG. 6 is a schematic diagram of the motional bridge 430 of FIGS. 4A and 4B, according to one aspect of the present disclosure. The ultrasonic transducer 440 includes piezoelectric material that converts the high voltage AC signal into mechanical motion. Motional bridge 430 is coupled to the ultrasonic transducer 440 and provides a motional feedback signal 431 that approximates the mechanical motion of the ultrasonic transducer 440 (see FIGS. 4A and 4B).

The motional bridge 430 measures a motional current, approximating the mechanical motion of the ultrasonic transducer 440, and provides a motional feedback signal 431 to the TAG microcontroller 322. The motional feedback signal 431 is a voltage signal corresponding to the motional current. The TAG microcontroller 322 uses the motional feedback signal 431 to adjust the frequency of the driving signal 419 to reach and maintain resonance of the ultrasonic transducer 440 (see FIGS. 4A and 4B).

Figure 7:
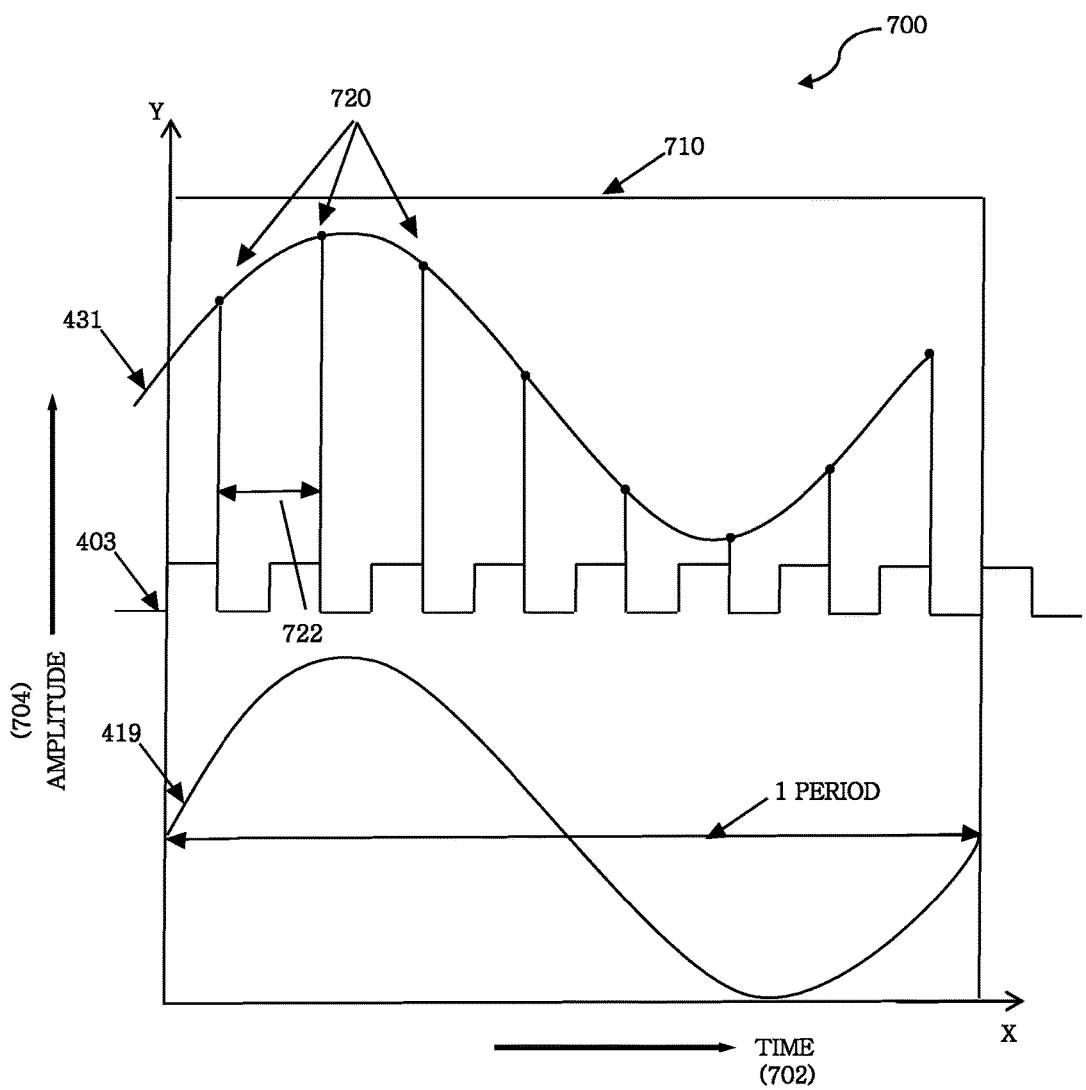
FIG. 7 is a graph illustrating coherent sampling, according to at least one aspect of the present disclosure.

FIG. 7 depicts a sample window 700 illustrating coherent sampling 710, according to at least one aspect of the present disclosure.

As described above, the A/D converter 416 of the TAG microcontroller 322 samples the motional feedback signal 431. The CLA 414, using the DFT algorithm 417, transforms these samples 720 to obtain phase and magnitude information relating to the motional feedback signal 431. The TAG microcontroller 322 uses a technique called coherent sampling to sample the motional feedback signal 431. According to this technique, the time interval 722 between samples is set to an integer multiple of one cycle of the driving signal. The sample window 700 illustrates the samples 720 across the motion feedback signal 431, with the x-axis representing time 702 and the y-axis representing amplitude 704.

The time interval 722 between samples is selected so that the A/D converter 416 samples the motional feedback signal 431 several times per cycle of the driving signal 419. In this way, the sample clock signal 403 and driving signal 419 are in phase. As a result, the driving signal 419 defines the reference point for calculating the phase of the sampled motional feedback signal 431 using the DFT algorithm 417.

After taking several samples of the motional feedback signal 431 according to the coherent sampling technique, the CLA 414 performs the DFT algorithm 417 on these samples 720. Specifically, the CLA 414 performs the DFT algorithm 417 to transform these samples 720, which are in the time-domain, into frequency-domain information. The frequency-domain information includes magnitude and phase information of the peak frequency response of the sampled motional feedback signal 431. This information is transferred from the CLA 414 to the main processor 412 of the TAG microcontroller 322. The main processor 412 uses the phase information to calculate a new frequency, which is used to set the frequency of the clock signal output 403 from the DDS 410.

Figure 8A:
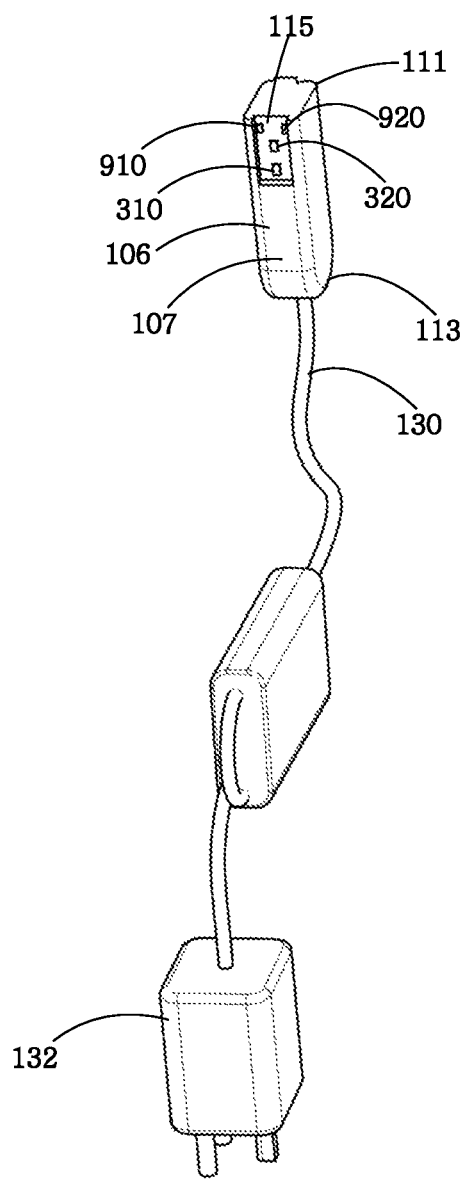
FIGS. 8A and 8B are perspective views of the handle assembly having a pair of electrical contacts, and the ultrasonic surgical device having another pair of contacts for permitting communicating therebetween, according to at least one aspect of the present disclosure.
Figure 8B:
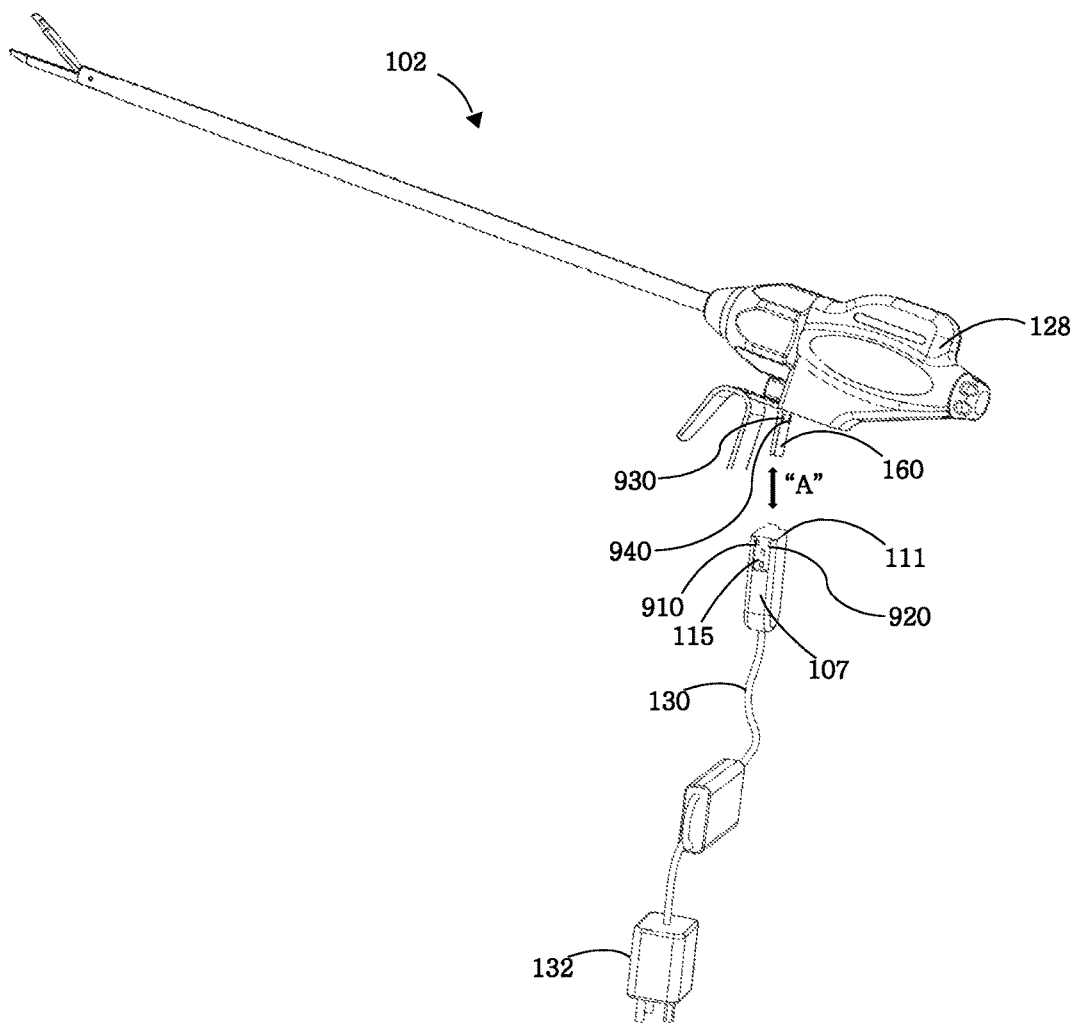

FIGS. 8A and 8B are perspective views of the handle assembly 106 having a pair of electrical contacts 910, 920, and the ultrasonic surgical device 102 having another pair of contacts 930, 940 for permitting communication therebetween, according to at least one aspect of the present disclosure.

In FIG. 8A, the handle assembly 106 includes a first electrical contact 910 and a second electrical contact 920. The electrical contacts 910, 920 are configured to electrically communicate "A" with two respective electrical contacts 930, 940 of TAG 128, as shown in FIG. 8B. The handle assembly 106 is detachably connected or removably coupled to the TAG 128 of the ultrasonic surgical instrument 102 via connection of the electrical contacts 910, 920, with contacts 930, 940. The electrical contacts 910, 920 may also be referred to as power contacts.

A first surface 107 of the housing assembly 106 is configured to accommodate the electrical contacts 910, 920 (FIG. 8A). The electrical contacts 910, 920 may be in opposed relation to each other on the first surface 107. The electrical contacts 910, 920 are positioned or placed at the proximalmost end 111 of the housing assembly 106. The distalmost end 113 of the housing assembly 106 is configured to connect to the cable 130 of the plug 132. The cable 130 may be a power cable. The electrical contacts 910, 920 are further placed on a recessed surface 115 of the proximalmost end 111 of the housing assembly 106. The recessed surface 115 is part of the first surface 107 of the housing assembly 106.

The generator of TAG 128 includes a contact connector 160. The contact connector 160 projects from the bottom portion 150 of the TAG 128. The contact connector 160 may be substantially perpendicular to the longitudinal axis "B-B" defined by the shaft 108 of the instrument 102. The contact connector 160 is adapted and dimensioned to connect with the recessed surface 115 of the first surface 107 of the housing assembly 106 in order to provide for an electrical connection between the electrical contacts 910, 920 of the housing assembly 106 and the electrical contacts 930, 940 of the contact connector 160 of the TAG 128. It is contemplated that the contact connector 160 slides into the recessed surface 115. Alternatively, it is contemplated that the contact connector 160 snaps into the recessed surface 115. One skilled in the art may contemplate a plurality of different connecting mechanisms for electrically connecting the electrical contacts 910, 920 with the electrical contacts 930, 940.

A user of the ultrasonic surgical instrument 102 may attach/detach any type of compatible handle assembly having a power receiving mechanism, such as a plug. The plug may be reusable. Alternatively, the plug may be disposable. The plug may be a U.S. style plug. The plug may also be a U.K./European style plug. The plug may be any type of conventional or non-conventional plug for receiving power from an outlet. The plug and power cable act as an alternative to using rechargeable batteries for powering the ultrasonic surgical instrument 102. As a result, the ultrasonic surgical instrument 102 may be connected to any electrical outlet to receive power without the need to charge/recharge batteries, as the instrument 102 is battery free. Further, TAG 128 is autoclavable. Autoclavable materials may be used to form TAG 128, and/or other components of the instrument 102, to provide for a sterilizable device.

Therefore, in summary, the power cable provides a means to power the ultrasonic surgical instrument, as an alternative to using rechargeable batteries. The power cable may be disposable or reusable. The AC/DC transformer converts electricity received from the plug into proper DC voltage and allows for isolation between the patient/user and any current levels.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An ultrasonic surgical instrument, comprising:
a housing;
an ultrasonic transducer and generator assembly disposed in the housing;
a shaft extending from a distal end of the housing;
an end effector assembly coupled to the shaft and operatively connected to the ultrasonic transducer and generator assembly;
a handle assembly having a first set of power contacts formed thereon and being removably attachable to the housing;
a power receiving mechanism having a second set of power contacts formed thereon; and
a power cable electrically connected between the first and second power contacts.

2. The ultrasonic surgical instrument according to claim 1, further including a waveguide mechanically coupled to the ultrasonic transducer and generator assembly and disposed in the shaft, the waveguide being adapted to transmit current from the power cable to the end effector assembly.

3. The ultrasonic surgical instrument according to claim 1, further including a microcontroller and a buck converter operatively connected to the ultrasonic transducer and generator assembly.

4. The ultrasonic surgical instrument according to claim 3, wherein the buck converter is a DC-DC converter board incorporating a synchronous two-phase buck converter.

5. The ultrasonic surgical instrument according to claim 3, wherein the buck converter receives an unregulated DC voltage from the power cable and supplies a regulated and reduced DC output voltage to the ultrasonic transducer and generator assembly.

6. The ultrasonic surgical instrument according to claim 3, wherein the microcontroller provides a pulse width modulation signal to the buck converter to regulate current supplied to the ultrasonic transducer and generator assembly via the power cable.

7. The ultrasonic surgical instrument according to claim 1, wherein the power receiving mechanism includes an AC/DC transformer.

8. The ultrasonic surgical instrument according to claim 1, wherein a clamp trigger is operatively associated with the end effector assembly.

9. The ultrasonic surgical instrument according to claim 1, wherein an activation button is operatively connected to the ultrasonic transducer and generator assembly.

10. The ultrasonic surgical instrument according to claim 9, wherein the activation button is a two-position activation button that initiates low- or high-power modes of operation.

11. The ultrasonic surgical instrument according to claim 1, wherein the ultrasonic transducer and generator assembly is configured to be autoclavable.

12. A method for performing a surgical procedure, the method comprising:
accessing an underlying operative site with an ultrasonic surgical instrument, including:
a housing;
an ultrasonic transducer and generator assembly disposed in the housing;
a shaft extending from a distal end of the housing;
an end effector assembly coupled to the shaft and operatively connected to the ultrasonic transducer and generator assembly;
a handle assembly having a first set of power contacts formed thereon and being removably attachable to the housing;
a power receiving mechanism having a second set of power contacts formed thereon; and
a power cable electrically connected between the first and second power contacts.

13. The method according to claim 12, further comprising mechanically coupling a waveguide to the ultrasonic transducer and generator assembly, the waveguide being adapted to transmit current from the power cable to the end effector assembly.

14. The method according to claim 13, further comprising transmitting current from the power cable to the ultrasonic transducer and generator assembly, which converts the current to a motional vibration imparted on a waveguide which transmits the motional vibration to the end effector assembly.

15. The method according to claim 12, further comprising providing a microcontroller and a buck converter in the housing.

16. The method according to claim 15, further comprising receiving, via the buck converter, an unregulated DC voltage from the power cable and supplying a regulated and reduced DC output voltage to the ultrasonic transducer and generator assembly.

17. The method according to claim 16, further comprising providing, via the microcontroller, a pulse width modulation signal to the buck converter to regulate current supplied to the ultrasonic transducer and generator assembly via the power cable.

18. The method according to claim 12, further comprising operatively associating a clamp trigger with the end effector assembly.

19. The method according to claim 12, further comprising operatively connecting an activation button to the ultrasonic transducer and generator assembly.

20. The method according to claim 19, wherein the activation button is a two-position activation button that initiates low- or high-power modes of operation.

* * * * *